(12) United States Patent
Yamada et al.

(10) Patent No.: US 9,420,794 B2
(45) Date of Patent: Aug. 23, 2016

(54) HERBICIDAL COMPOSITION

(71) Applicant: ISHIHARA SANGYO KAISHA, LTD., Osaka (JP)

(72) Inventors: Ryu Yamada, Shiga (JP); Hiroyuki Okamoto, Shiga (JP); Takashi Terada, Shiga (JP)

(73) Assignee: ISHIHARA SANGYO KAISHA, LTD., Osaka (JP)

( * ) Notice: Subject to any disclaimer, the term of this patent is extended or adjusted under 35 U.S.C. 154(b) by 0 days.

(21) Appl. No.: 14/401,996

(22) PCT Filed: May 28, 2013

(86) PCT No.: PCT/JP2013/064768
§ 371 (c)(1),
(2) Date: Nov. 18, 2014

(87) PCT Pub. No.: WO2013/180129
PCT Pub. Date: Dec. 5, 2013

(65) Prior Publication Data
US 2015/0133300 A1    May 14, 2015

(30) Foreign Application Priority Data
May 28, 2012 (JP) .................. 2012-120607

(51) Int. Cl.
*A01N 47/36* (2006.01)
*A01N 43/80* (2006.01)
*A01N 43/10* (2006.01)

(52) U.S. Cl.
CPC ............... *A01N 47/36* (2013.01); *A01N 43/10* (2013.01); *A01N 43/80* (2013.01)

(58) Field of Classification Search
CPC combination set(s) only.
See application file for complete search history.

(56) References Cited

U.S. PATENT DOCUMENTS

| | | | |
|---|---|---|---|
| 5,457,085 A * | 10/1995 | Seckinger et al. | ............ 504/289 |
| 6,534,444 B1 | 3/2003 | Sievernich et al. | |
| 7,842,646 B2 | 11/2010 | Sievernich et al. | |
| 8,017,556 B2 | 9/2011 | Gebhardt et al. | |
| 2003/0203819 A1 | 10/2003 | Sievernich et al. | |
| 2005/0239653 A1 | 10/2005 | Sievernich et al. | |
| 2007/0123426 A1 | 5/2007 | Vantieghem et al. | |
| 2010/0227763 A1 | 9/2010 | Krapp et al. | |
| 2011/0015069 A1 | 1/2011 | Sievernich et al. | |

FOREIGN PATENT DOCUMENTS

| | | |
|---|---|---|
| EP | 1 087 664 | 4/2001 |
| EP | 1 338 199 | 8/2003 |
| JP | 2009-517365 | 4/2009 |
| JP | 2009-545571 | 12/2009 |
| JP | 2010-532333 | 10/2010 |
| JP | 2011-515356 | 5/2011 |
| WO | 99/65314 | 12/1999 |
| WO | 2007/060146 | 5/2007 |
| WO | 2008/015279 | 2/2008 |
| WO | 2009/007329 | 1/2009 |
| WO | 2009/115433 | 9/2009 |

OTHER PUBLICATIONS

International Search Report of Patent Application No. PCT/JP2013/064768 mailed Aug. 13, 2013; along with an English Translation thereof.
International Preliminary Report on Patentability PCT/JP2013/064768, dated Dec. 11, 2014.
Maurath, "Ergebnisse zu HGV-Maisherbizidversuchen im Rheintal 2009", Bildungszentrum EM-Hochburg, Feb. 2010 (17 pages).

* cited by examiner

*Primary Examiner* — John Pak
(74) *Attorney, Agent, or Firm* — Greenblum & Bernstein, P.L.C.

(57) ABSTRACT

To provide a high active herbicidal composition having a broader herbicidal spectrum against a wide variety of weeds to be controlled.
A herbicidal composition comprising (a) nicosulfuron or its salt, (b) dimethenamid-P or its salt and (c) topramezone or its salt. This herbicidal composition has a wide herbicidal spectrum and has high activity.

8 Claims, No Drawings

HERBICIDAL COMPOSITION

TECHNICAL FIELD

The present invention relates to a herbicidal composition comprising (a) nicosulfuron or its salt (hereinafter referred to as compound A), (b) dimethenamid-P or its salt (hereinafter referred to as compound B) and (c) topramezone or its salt (hereinafter referred to as compound C).

BACKGROUND ART

Patent Document 1 discloses a method for controlling undesired plants, which comprises applying dimethenamid and at least one other herbicide selected from amino acid synthesis inhibitors to the undesired plants.

Patent Document 2 discloses a synergistic herbicidal composition comprising a 3-heterocyclyl-substituted benzoyl derivative and a specific herbicide.

However, either of the above Patent Documents does not disclose a specific combination of compound A, compound B and compound C which are herbicidally active ingredients of the present invention, and does not specifically disclose a remarkable synergistic effect obtained by the combination.

PRIOR ART DOCUMENTS

Patent Documents

Patent Document 1: EP1338199
Patent Document 2: EP1087664

DISCLOSURE OF INVENTION

Technical Problem

At present, many herbicidal compositions have been developed and used, but there are a variety of types of undesired plants represented by weeds to be controlled. Further, undesired plants having lowered sensitivity to herbicides (herbicide-resistant weeds) emerged, and in some applications, practically, herbicides have only insufficient effects.

The object of the present invention is to provide a high active herbicidal composition having a broader herbicidal spectrum, and a method for controlling undesired plants or inhibiting their growth using it.

Solution to Problem

The present inventors have conducted extensive studies to solve the above problems and as a result, found that unexpectedly excellent herbicidal effects can be obtained by combination of specific compound A, compound B and compound C which are herbicidally active ingredients of the present invention, as compared with a case where the respective compounds are applied individually or two compounds are used in combination (for example, compound A and compound C are used in combination), and accomplished the present invention.

That is, the present invention provides the following.

(1) A herbicidal composition comprising (a) nicosulfuron or its salt, (b) dimethenamid-P or its salt and (c) topramezone or its salt.

(2) The herbicidal composition according to the above (1), wherein the mixing ratio of (a) to (b) is from 1:1.3 to 1:400 by the weight ratio, and the mixing ratio of (a) to (c) is from 15:1 to 1:30 by the weight ratio.

(3) The herbicidal composition according to the above (1), which is used to control *convolvulaceae, solanaceae, gramineae, malvaceae, compositae* or *leguminosae*, or to inhibit their growth.

(4) A method for controlling undesired plants or inhibiting their growth, which comprises applying a herbicidally effective amount of (a) nicosulfuron or its salt, a herbicidally effective amount of (b) dimethenamid-P or its salt, and a herbicidally effective amount of (c) topramezone or its salt, to the undesired plants or to a place where they grow.

(5) The method according to the above (4), wherein (a) is applied in an amount of from 5 to 150 g/ha, (b) is applied in an amount of from 200 to 2,000 g/ha, and (c) is applied in an amount of from 10 to 150 g/ha.

(6) The method according to the above (4), wherein the undesired plants are *convolvulaceae, solanaceae, gramineae, malvaceae, compositae* or *leguminosae*.

(7) The method according to the above (4), wherein the undesired plants are *gramineae, malvaceae, compositae* or *lequminosae*.

(8) The method according to the above (4), wherein the undesired plants are annual or perennial *gramineae*.

(9) The method according to the above (4), wherein the undesired plants are strongly noxious weeds in corn fields.

Advantageous Effects of Invention

The herbicidal composition of the present invention is capable of controlling a wide range of undesired plants emerging in agricultural fields or non-agricultural fields. It represents a synergistic effect i.e. a herbicidal effect higher than the mere addition of the herbicidal effects of the respective active ingredients applied individually.

Such a herbicidal composition of the present invention can be applied at a low dose as compared with a case where the respective active ingredients are applied individually. Thus, it is effective to reduce the environmental load on an area where the composition is applied or a surrounding area thereof.

The herbicidal composition of the present invention has a remarkable herbicidal activity (1) when a composition comprising compound A and compound B, and compound C are used in combination, (2) when a composition comprising compound B and compound C, and compound A are used in combination, and (3) when a composition comprising compound A and compound C, and compound B are used in combination. It represents a synergistic effect i.e. a herbicidal effect higher than the mere addition of the herbicidal effect of the combination of a first herbicidally active ingredient and a second herbicidally active ingredient and the herbicidal effect of a third herbicidally active ingredient.

When the herbicidal activity in a case where two active ingredients are combined, is larger than the simple sum of the respective herbicidal activities of the two active ingredients (the expected activity), it is called a synergistic effect.

The activity expected by the combination of two active ingredients can be calculated as follows (Colby S. R., "Weed", vol. 15, p. 20-22, 1967).

$$E^1 = (\alpha+\beta) - (\alpha\beta)/100$$

Similarly, the activity expected by the combination of three active ingredients can be calculated as follows.

$$E^2 = (\alpha+\beta+\gamma) - (\alpha\beta+\alpha\gamma+\beta\gamma)/100 + (\alpha\beta\gamma)/10,000$$

where α: growth inhibition rate when treated with x (g/ha) of herbicide X,

βR: growth inhibition rate when treated with y (g/ha) of herbicide Y,

γ: growth inhibition rate when treated with z (g/ha) of herbicide Z, $E^1$: growth inhibition rate expected when treated with x (g/ha) of herbicide X and y (g/ha) of herbicide Y.

$E^2$: growth inhibition rate expected when treated with x (g/ha) of herbicide X, y (g/ha) of herbicide Y, and z (g/ha) of herbicide Z.

That is, when the actual growth inhibition rate (measured value) is larger than the growth inhibition rate by the above calculation (calculated value), the activity by the combination can be regarded as showing a synergistic effect.

The herbicidal composition of the present invention shows a synergistic effect when calculated by the above formula.

DESCRIPTION OF EMBODIMENTS

As for compound A, nicosulfuron (common name) is 2-(4,6-dimethoxypyrimidin-2-ylcarbamoylsulfamoyl)-N,N-dimethylnicotinamide.

As for compound B, dimethenamid-P (common name) is (S)-2-chloro-N-(2,4-dimethyl-3-thienyl)-N-(2-methoxy-1-methylethyl)acetamide.

As for compound C, topramezone (common name) is [3-(4,5-dihydro-1,2-oxazol-3-yl)-4-mesyl-o-tolyl](5-hydroxy-1-methylpyrazol-4-yl)methanone.

The salt included in compound A, compound B and compound C may be any salt so long as it is agriculturally acceptable. Examples thereof include alkali metal salts such as a sodium salt and a potassium salt; alkaline earth metal salts such as a magnesium salt and a calcium salt; ammonium salts such as a monomethylammonium salt, a dimethylammonium salt and a triethylammonium salt; inorganic acid salts such as a hydrochloride, a perchlorate, a sulfate and a nitrate, and organic acid salts such as an acetate and a methanesulfonate.

The mixing ratio of the respective compounds in the present invention cannot generally be defined, as it varies depending upon various conditions such as the type of the formulation, the weather conditions, and the type and the growth stage of the undesired plants. The mixing ratio of compound A to compound B is, for example, from 1:1.3 to 1:400, preferably from 1:2.5 to 1:150 by the weight ratio, and the mixing ratio of compound A to compound C is, for example, from 15:1 to 1:30, preferably from 6.7:1 to 1:10 by the weight ratio.

The herbicidally effective amounts of compounds A, B and C cannot generally be defined, as they vary depending upon various conditions such as the mixing ratios of the respective compounds, the type of the formulation, the weather conditions, and the type and the growth stage of the undesired plants. For example, compound A is applied in an amount of from 5 to 150 g/ha, preferably from 10 to 100 g/ha, compound B is applied in an amount of from 200 to 2,000 g/ha, preferably from 250 to 1,500 g/ha, and compound C is applied in an amount of from 10 to 150 g/ha, preferably from 15 to 100 g/ha.

The herbicidal composition of the present invention may be applied to undesired plants or may be applied to a place where they grow. Further, it may be applied at any time either before or after the emergence of the undesired plants.

Further, the herbicidal composition of the present invention may take various application forms such as soil application, foliar application, irrigation application, and submerged application, and it can be applied to agricultural fields such as upland fields, orchards and paddy fields, and non-cropland such as ridges of fields, fallow fields, play grounds, golf courses, vacant lands, forests, factory sites, railway sides and roadsides.

The herbicidal composition of the present invention can control a wide range of undesired plants such as annual weeds and perennial weeds. The undesired plants to be controlled by the herbicidal composition of the present invention may, for example, be specifically *cyperaceae* such as sedge (*Cyperus* spp.) (such as purple nutsedge (*Cyperus rotundus* L.), small-flower umbrella sedge (*Cyperus difformis* L.), yellow nutsedge (*Cyperus esculentus* L.) or amur *cyperus* (*Cyperus microiria* Steud.)) or spikesedge (*Kyllinga* spp.) (such as green *kyllinga* (*Kyllinga brevifolia* Rottb. var. *leiolepis*)); *gramineae* such as barnyard grass (*Echinochloa* spp.) (such as barnyardgrass (*Echinochloa crus-galli* L.), early watergrass (*Echinochloa oryzicola* vasing.) or Japanese millet (*Echinochloa utilis* Ohwi et Yabuno)), crabgrass (*Digitaria* spp.) (such as summergrass (*Digitaria ciliaris* (Retz.) Koel), large crabgrass (*Digitaria sanguinalis* L.), violet crabgrass (*Digitaria violascens* Link) or Jamaican crabgrass (*Digitaria horizontalis* Willd.)), goosegrass (*Eleusine* spp.) (such as goosegrass (*Eleusine indica* L.)), ryegrass (*Lolium* spp.) (such as italian ryegrass (*Lolium multiflorum* Lam.)), foxtail (*Setaria* spp.) (such as green foxtail (*Setaria viridis* (L.))), sorghum (*Sorghum* spp.) (such as johnsongrass (*Sorghum halepense* (L.) Pers.) or shattercane (*Sorghum bicolor* (L.) Moench.)), oat (*Avena* spp.) (such as wild oat (*Avena fatua* L.)), brome (*Bromus* spp.) (such as drooping brome (*Bromus tectorum* L.) or japanese brome (*Bromus japonicus* Thunb.)), meadowgrass (*Poa* spp.) (such as annual bluegrass (*Poa annus* L.)), foxtail grass (*Alopecurus* spp.) (such as blackgrass (*Alopecurus myosuroides* Huds.), shortawn foxtail (*Alopecurus aequalis* Sobol. var. amurensis)), bermudagrass (*Cynodon dactylon* (L.) Pers.), panic grass (*Panicum* spp.) (such as guinea grass (*Panicum maximum* Jacq.) or fall *panicum* (*Panicum dichotomiflorum* (L.) Michx.)), signal grass (*Brachiaria* spp.) (such as plantain signal grass (*Brachiaria plantaginea* (LINK) Hitchc.), palisade signal grass (*Brachiaria decumbens* Stapf) or mauritius signal grass (*Brachiaria mutica* (Forssk.) Stapf)), *paspalum* (*Paspalum* spp.) (such as dallisgrass (*Paspalum dilatatum* Poir.) or vasey's grass (*Paspalum urvillei* Steud.)), itchgrass (*Rottboellia* spp.) (such as itchgrass (*Rottboellia cochinchinensis* (LOUR.) W. D. CLAYTON)), or sandbur (*Cenchrus* spp.) (such as southern sandbur (*Cenchrus echinatus* L.)); scrophulariaceae such as persian speedwell (*Veronica persica* Poir.) or corn speedwell (*Veronica arvensis* L.); compositae such as beggar ticks (*Bidens* spp.) (such as hairy beggarticks (*Bidens pilosa* L.), devils berggarticks (*Bidens frondosa* L.) or *Bidens biternata* (Lour.) Merr. et Sherff, beggarticks (*Bidens subalternans* DC.)), hairy fleabane (*Conyza bonariensis* (L.) Cronq.), dandelion (*Taraxacum officinale* Weber), horseweed (*Conyza* spp.) (such as canadian horseweed (*Conyza canadensis* (L.) Cronquist)), cocklebur (*Xanthium* spp.) (such as common cocklebur (*Xanthium strumarium* L.)), ragweed (*Ambrosia* spp.) (such as annual ragweed (*Ambrosia artemisiifolia* L.)), ragwort (*Senecio* spp.) (such as old-man-in-the-spring (*Senecio vulgaris* L.)); leguminosae such as rattlepod or rattlebox (*Crotalaria* spp.) (such as sunn-hemp (*Crotalaria juncea* L.)), poison bean (*Sesbania* spp.) (such as rostrate *sesbania* (*Sesbania rostrata* Bremek. & Oberm.) or *sesbania* pea (*Sesbania cannabina* (Retz.) Pers.)), korean lespedeza (*Kummerowia stipulacea* (Maxim.) Makino) or white clover (*Trifolium repens* L.)); caryophyllaceae such as sticky chickweed (*Cerastium glomeratum* Thuill.) or starwort (*Stellaria* spp.) (such as common chickweed (*Stellaria media* L.)); euphorbiaceae such as garden spurge (*Euphorbia hirta* L.), three-seeded copperleaf (*Acalypha australis* L.) or fireplant (*Euphorbia heterophylla* L.); plantaginaceae such as asiatic plantain (*Plantago asiatica* L.); oxalidaceae such as creeping woodsorrel (*Oxalis corniculata* L.); apiaceae such as lawn pennywort (*Hydrocotyle sibthorpioides* Lam.); violaceae such as violet (*Viola mandshurica* W. Becker): iridaceae such as blue-eyedgrass (*Sisyrinchium rosulatum* Bicknell); geraniaceae such as carolina geranium (*Geranium carolinianum* L.); labiatae such as purple deadnettle (*Lamium purpureum* L.) or henbit (*Lamium amplexicaule* L.); malvaceae such as velvetleaf (*Abutilon theophrasti* MEDIC.) or prickly sida (*Sida spinosa* L.); convolvulaceae such as ivy-leaved morninggglory (*Ipomoea hederacea* (L.)

Jacq.), common morninggglory (*Ipomoea purpurea* ROTH), cypressvine morninggglory (*Ipomoea quamoclit* L.), *Ipomoea grandifolia* (DAMMERMANN) O'DONNELL, hairy merremia (*Merremia aeqyptia* (L.) URBAN) or field bindweed (*Convolvulus arvensis* L.); chenopodiaceae such as goosefoot (*Chenopodium* spp.) (such as common lambsquarters (*Chenopodium album* L.)); portulacaceae such as common purslane (*Portulaca oleracea* L.); amaranthaceae such as pigweed (*Amaranthus* spp.) (such as prostrate pigweed (*Amaranthus blitoides* S. Wats.), livid amaranth (*Amaranthus lividus* L.), purple amaranth (*Amaranthus blitum* L.), smooth pigweed (*Amaranthus hybridus* L., *Amaranthus patulus* Bertol.), powell amaranth (*Amaranthus powellii* S. Wats.), slender amaranth (*Amaranthus viridis* L.), palmer amaranth (*Amaranthus palmeri* S. Wats.), redroot pigweed (*Amaranthus retroflexus* L.), tall waterhemp (*Amaranthus tuberculatus* (Moq.) Sauer.), common waterhemp (*Amaranthus tamariscinus* Nutt.), thorny amaranth (*Amaranthus spinosus* L.)), ataco (*Amaranthus quitensis* Kunth.) or roughfruit amaranth (*Amaranthus rudis* Sauer.)); solanaceae such as nightshade (*Solanum* spp.) (such as black nightshade (*Solanum nigrum* L.)); polygonaceae such as knotweed (*Polygonum* spp.) (such as spotted knotweed (*Polygonum lapathifolium* L.) or green smartweed (*Polygonum scabrum* MOENCH)); cruciferae such as flexuous bittercress (*Cardamine flexuosa* WITH.), or mustard (*Sinapis* spp.) (such as Charlock (*Sinapis arvensis* L.)); cucurbitaceae such as burcucumber (*Sicyos angulatus* L.); commelinaceae such as common dayflower (*Commelina communis* L.); rosaceae such as mock strawberry (*Duchesnea chrysantha* (Zoll. et Mor.) Miq.); molluginacea such as carpetweed (*Mollugo verticillata* L.); or rubiaceae such as false cleavers (*Galium spurium* var. echinospermon (Wallr.) Hayek) or stickywilly (*Galium aparine* L.).

The herbicidal composition of the present invention is very useful in practical application. For example, the following cases may be mentioned.

(1) It has a remarkable synergistic effect, and has a favorable herbicidal activity even if the doses of the respective compounds A, B and C are small, and accordingly the impact on the surrounding environment can be suppressed.

(2) A herbicidal composition has a long lasting residual activity, as compared with a case where compound A, compound B and compound C are applied individually, or two compounds are used in combination (for example, compound A and compound B are used in combination). That is, a herbicidal composition having a long lasting herbicidal effect may be provided in some cases.

(3) A herbicidal composition having a broad herbicidal spectrum having high effects against both *gramineae* and broad leaf weeds, as compared with a case where compound A, compound B and compound C are applied individually, or two compounds are used in combination (for example, compound A and compound B are used in combination), may be provided in some cases.

(4) Emergence of herbicide-resistant weeds or low sensitive weeds may be suppressed in some cases as compared with a case where compound A, compound B and compound C are applied individually, or two compounds are used in combination (for example, compound A and compound B are used in combination).

(5) Annual and perennial *gramineae* such as *Echinochloa* spp., *Digitaria* spp., *Setaria* spp., *Poa* spp., *Avena* spp., *Agropyron* spp., *Alopecurus* spp., *Eleusine* spp., *Rottboellia* spp., *Sorghum* spp. and *Panicum* spp., which are problematic as noxious weeds in agricultural fields, particularly corn fields, can be controlled.

(6) A herbicidal composition which may be applied at any time from soil treatment to foliar treatment in late leaf stage may be provided in some cases as compared with a case where compound A, compound B and compound C are applied individually, or two compounds are used in combination (for example, compound A and compound B are used in combination).

In consideration of the application site of the herbicidal composition or the type or growth state of the undesired plants, the herbicidal composition of the present invention may be mixed with or may be used in combination with other herbicides, fungicides, antibiotics, plant hormones, insecticides, fertilizers, phytotoxicity-reducing agents, etc., in addition to the above active ingredients, without departing from the intention and the scope of the present invention, whereby more excellent effects and activities may sometimes be obtained.

Such other herbicides may, for example, be (1) those which are believed to exhibit herbicidal effects by disturbing hormone activities of plants, (2) those which are believed to exhibit herbicidal effects by inhibiting photosynthesis of plants, (3) those which are believed to be converted to free radicals by themselves to form active oxygen in the plant body and show rapid herbicidal efficacy, (4) those which are believed to exhibit herbicidal effects by inhibiting chlorophyll biosynthesis of plants and abnormally accumulating a photosensitizing peroxide substance in the plant body, (5) those which are believed to exhibit herbicidal effects characterized by bleaching activities by inhibiting chromogenesis of plants such as carotenoids, (6) those which exhibit strong herbicidal effects specifically to gramineous plants, (7) those which are believed to exhibit herbicidal effects by inhibiting an amino acid biosynthesis of plants, (8) those which are believed to exhibit herbicidal effects by inhibiting cell mitoses of plants, (9) those which are believed to exhibit herbicidal effects by inhibiting protein biosynthesis or lipid biosynthesis of plants, and (10) those which are believed to exhibit herbicidal effects by being parasitic on plants.

The herbicidal composition of the present invention may be prepared by mixing compound A, compound B and compound C, as active ingredients, with various agricultural additives in accordance with conventional formulation methods for agricultural chemicals, and applied in various formulations such as dusts, granules, water dispersible granules, wettable powders, tablets, pills, capsules (including a formulation packaged by a water soluble film), water-based suspensions, oil-based suspensions, microemulsions, suspoemulsions, water soluble powders, emulsifiable concentrates, soluble concentrates or pastes. That is, it may be formed into any formulation which is commonly used in this field, so long as the object of the present invention is thereby met.

At the time of the formulation, compound A, compound B and compound C may be mixed together for the formulation, or they may be separately formulated.

The additives to be used for the formulation include, for example, a solid carrier such as kaolinite, sericite, diatomaceous earth, slaked lime, calcium carbonate, talc, white carbon, kaoline, bentonite, clay, sodium carbonate, sodium bicarbonate, mirabilite, zeolite or starch; a solvent such as water, toluene, xylene, solvent naphtha, dioxane, dimethylsulfoxide, N,N-dimethylformamide, dimethylacetamide, N-methyl-2-pyrrolidone or an alcohol; an anionic surfactant such as a salt of fatty acid, a benzoate, a polycarboxylate, a salt of alkylsulfuric acid ester, an alkyl sulfate, an alkylaryl sulfate, an alkyl diglycol ether sulfate, a salt of alcohol sulfuric acid ester, an alkyl sulfonate, an alkylaryl sulfonate, an aryl sulfonate, a lignin sulfonate, an alkyldiphenylether disulfonate, a polystyrene sulfonate, a salt of alkylphosphoric acid ester, an alkylaryl phosphate, a styrylaryl phosphate, a salt of polyoxyethylene alkyl ether sulfuric acid ester, a polyoxyethylene alkylaryl ether sulfate, a salt of polyoxyethylene alkylaryl ether sulfuric acid ester, a polyoxyethylene alkyl ether phosphate, a salt of polyoxyethylene alkylaryl phosphoric acid ester, a salt of polyoxyethylene aryl ether phosphoric acid ester, a naphthalene sulfonic acid condensed with formaldehyde or a salt of alkylnaphthalene sulfonic acid condensed with formaldehyde; a nonionic surfactant such as a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, polyethylene glycol, a polyoxyethylene fatty acid ester, a polyoxyethylene sorbitan fatty acid ester, a polyoxyethylene glycerin fatty acid ester, a polyoxyethylene hydrogenated castor oil or a polyoxypropylene fatty acid ester; a vegetable oil or mineral oil such as olive oil, kapok oil, castor oil, palm oil, camellia oil, coconut oil, sesame oil, corn oil, rice bran oil, peanut oil, cottonseed oil, soybean oil, rapeseed oil, linseed oil, tung oil or liquid paraffins; and a transesterified vegetable oil such as methylated rapeseed oil or ethylated rapeseed oil. These additives may suitably be selected for use alone or in combination as a mixture of two or more of them, so long as the object of the present invention is met. Further, additives other than the above-mentioned may be suitably selected for use among those known in this field. For example, various additives commonly used, such as a filler, a thickener, an anti-settling agent, an anti-freezing agent, a dispersion stabilizer, a safener, an anti-mold agent, a bubble agent, a disintegrator and a binder, may be used. The mix ratio by weight of the active ingredients to such various additives in the herbicidal composition of the present invention may be from 0.001:99.999 to 95:5, preferably from about 0.005:99.995 to about 90:10.

As a method of applying the herbicidal composition of the present invention, a proper method can be employed among various methods depending upon various conditions such as the application site, the type of the formulation, and the type and the growth stage of the undesired plants to be controlled, and for example, the following methods may be mentioned.

(1) Compound A, compound B and compound C are separately formulated, and the formulations are applied to plants to be controlled as they are or as diluted to predetermined concentrations with e.g. water, and as the case requires, as mixed with a spreader (such as a surfactant, a vegetable oil or a mineral oil).

(2-1) Compound A and compound B are formulated together, and compound C is formulated, and the formulations are applied to plants to be controlled as they are or as diluted to predetermined concentrations with e.g. water, and as the case requires, as mixed with a spreader (such as a surfactant, a vegetable oil or a mineral oil).

(2-2) Compound A and compound C are formulated together, and compound B is formulated, and the formulations are applied to plants to be controlled as they are or as diluted to predetermined concentrations with e.g. water, and as the case requires, as mixed with a spreader (such as a surfactant, a vegetable oil or a mineral oil).

(2-3) Compound B and compound C are formulated together, and compound A is formulated, and the formulations are applied to plants to be controlled as they are or as diluted to predetermined concentrations with e.g. water, and as the case requires, as mixed with a spreader (such as a surfactant, a vegetable oil or a mineral oil).

(3) Compound A, compound B and compound C are formulated together, and the formulation is applied to plants to be controlled as it is or as diluted to a predetermined concentration with e.g. water, and as the case requires, as mixed with a spreader (such as a surfactant, a vegetable oil or a mineral oil).

In the above application methods (1) and (2-1) to (2-3), the respective formulations may be mixed when diluted to predetermined concentrations with e.g. water so that they are applied to plants to be controlled simultaneously, or they may be applied continuously or with an appropriate interval. In order to obtain effects of the present invention more effectively, it is preferred to apply compound A, compound B and compound C simultaneously.

Preferred embodiments of the present invention will be described below, but the present invention is by no means restricted thereto.

(1) A herbicidal composition comprising (a) nicosulfuron or its salt, (b) dimethenamid-P or its salt and (c) topramezone or its salt.

(2) The herbicidal composition according to the above (1), which contains (a), (b) and (c) in amounts to show a herbicidally synergistic effect (synergistic herbicidally effective amounts).

(3) The herbicidal composition according to the above (1), wherein the weight ratio of (a) to (b) is within a range of from 1:1.3 to 1:400, and the weight ratio of (a) to (c) is within a range of from 15:1 to 1:30.

(4) The herbicidal composition according to the above (1), wherein the weight ratio of (a) to (b) is within a range of from 1:2.5 to 1:150, and the weight ratio of (a) to (c) is within a range of from 6.7:1 to 1:10.

(5) A method for controlling undesired plants or inhibiting their growth, which comprises applying a herbicidally effective amount of a herbicidal composition comprising (a), (b) and (c), to the undesired plants or to a place where they grow.

(6) A method for controlling undesired plants or inhibiting their growth, which comprises applying a herbicidally effective amount of (a), a herbicidally effective amount of (b) and a herbicidally effective amount of (c) to the undesired plants or to a place where they grow.

(7) The method according to the above (5) or (6), wherein the undesired plants are weeds having lowered sensitivity to herbicidal compounds.

(8) The method according to the above (5) or (6), wherein the undesired plants are weeds having lowered sensitivity to ALS (acetolactate synthase) inhibitors.

(9) The method according to the above (5) or (6), which comprises applying (a) in an amount to show a herbicidally synergistic effect (synergistic herbicidally effective amount), (b) in an amount to show a herbicidally synergistic effect (synergistic herbicidally effective amount) and (c) in an amount to show a herbicidally synergistic effect (synergistic herbicidally effective amount).

(10) The method according to the above (5) or (6), wherein (a) is applied in an amount of from 5 to 150 g/ha, (b) is applied in an amount of from 200 to 2,000 g/ha, and (c) is applied in an amount of from 10 to 150 g/ha.

(11) The method according to the above (5) or (6), wherein (a) is applied in an amount of from 10 to 100 g/ha, (b) is applied in an amount of from 250 to 1,500 g/ha, and (c) is applied in an amount of from 15 to 100 g/ha.

(12) The herbicidal composition according to the above (1), which further contains (d) an additive for formulation which does not have a herbicidal effect by itself.

(13) The herbicidal composition according to the above (12), wherein (d) the additive for formulation is at least one member selected from the group consisting of a surfactant, a carrier, a solvent, a vegetable oil, a mineral oil and a transesterified vegetable oil.

(14) The herbicidal composition according to the above (1), which is used to control convolvulaceae, solanaceae, gramineae, malvaceae, compositae or leguminosae, or to inhibit their growth.

(15) The herbicidal composition according to the above (1), which is used to control gramineae, malvaceae, compositae or leguminosae, or to inhibit their growth.

(16) The herbicidal composition according to the above (1), which contains, as herbicidally active ingredients, only (a), (b) and (c).

(17) The method according to the above (5) or (6), wherein the undesired plants are convolvulaceae, solanaceae, gramineae, malvaceae, compositae or lequminosae.

(18) The method according to the above (5) or (6), wherein the undesired plants are gramineae, malvaceae, compositae or lequminosae.

EXAMPLES

Now, the present invention will be described in detail with reference to the following Examples. However, it should be understood that the present invention is by no means restricted thereto.

Test Example 1

Upland field soil was put into a 1/300,000 ha pot, and seeds of velvetleaf (*Abutilon theophrasti* Medic.) were sown. On the next day, predetermined amounts of a flowable containing nicosulfuron as an active ingredient (tradename: ONEHOPE NYUZAI, manufactured by Ishihara Sangyo Kaisha, Ltd.), an emulsifiable concentrate containing dimethenamid-P as an active ingredient (tradename: Spectrum, manufactured by BASF) and a flowable containing topramezone as an active ingredient (tradename: Clio, manufactured by BASF) were diluted with water (in an amount corresponding to 1,000 L/ha) and applied for soil treatment by a small sprayer.

On the 28th day after treatment, the state of growth of the velvetleaf was visually observed to determine the growth inhibition rate (%) in accordance with the following evaluation standard. The growth inhibition rate (%) (measured value) and the growth inhibition rate (%) (calculated value) calculated by the Colby's formula are shown in Table 1.

Growth inhibition rate (%)=0 (equivalent to the non-treated area) to 100 (complete kill)

TABLE 1

| | | Growth inhibition rate of velvetleaf (%) | |
|---|---|---|---|
| Compound | Dose (g/ha) | Measured value | Calculated value |
| Nicosulfuron | 15 | 0 | — |
| Dimethenamid-P | 500 | 20 | — |
| Topramezone | 20 | 60 | — |
| Nicosulfuron + Dimethenamid-P + Topramezone | 15 + 500 + 20 | 80 | 68 |

Test Example 2

Upland field soil was put into a 1/160,000 ha pot, and seeds of korean lespedeza (Kummerowia *stipulacea* (Maxim.) Makino) were sown. On the next day, predetermined amounts of ONEHOPE NYUZAI (tradename), Clio (tradename) and Spectrum (tradename) were diluted with water (in an amount corresponding to 300 L/ha) and applied for soil treatment by a small sprayer.

On the 14th day after treatment, the state of growth of the korean lespedeza was visually observed to determine the growth inhibition rate (%). The growth inhibition rate (%) (measured value) and the growth inhibition rate (%) calculated in the same manner as in the above Test Example 1 are shown in Table 2.

TABLE 2

| | | Growth inhibition rate of korean lespedeza (%) | |
|---|---|---|---|
| Compound | Dose (g/ha) | Measured value | Calculated value |
| Nicosulfuron | 10 | 0 | — |
| | 100 | 10 | — |
| Dimethenamid-P | 250 | 30 | — |
| | 1500 | 30 | — |
| Topramezone | 15 | 0 | — |
| | 100 | 10 | — |
| (Nicosulfuron + Dimethenamid-P) | (10 + 1500) | 40 | — |
| | (100 + 250) | 40 | — |
| (Nicosulfuron + Dimethenamid-P) + Topramezone | (10 + 1500) + 100 | 60 | 46 |
| | (100 + 250) + 15 | 60 | 40 |
| (Dimethenamid-P + Topramezone) | (250 + 15) | 30 | — |
| | (1500 + 100) | 50 | — |
| (Dimethenamid-P + Topramezone) + Nicosulfuron | (250 + 15) + 100 | 60 | 37 |
| | (1500 + 100) + 10 | 60 | 50 |
| (Nicosulfuron + Topramezone) | (10 + 100) | 25 | — |
| | (100 + 15) | 25 | — |
| (Nicosulfuron + Topramezone) + Dimethenamid-P | (10 + 100) + 1500 | 60 | 48 |
| | (100 + 15) + 250 | 60 | 48 |

Test Example 3

Upland field soil was put into a 1/1,000,000 ha pot, and seeds of annual ragweed (*Ambrosia artemisiifolia* L.) were sown. When the annual ragweed reached 6.0 to 8.0-leaf stage, predetermined amounts of ONEHOPE NYUZAI (tradename), Clio (tradename) and Spectrum (tradename) were diluted with water (in an amount corresponding to 300 L/ha) and applied for foliar treatment by a small sprayer.

On the 20 th day after treatment, the state of growth of the annual ragweed was visually observed to determine the growth inhibition rate (%). The growth inhibition rate (%) (measured value) and the growth inhibition rate (%) calculated in the same manner as in the above Test Example 1 are shown in Table 3.

TABLE 3

| Compound | Dose (g/ha) | Growth inhibition rate of annual ragweed (%) | |
|---|---|---|---|
| | | Measured value | Calculated value |
| Nicosulfuron | 30 | 13 | — |
| Topramezone | 20 | 40 | — |
| | 50 | 65 | — |
| Dimethenamid-P | 500 | 0 | — |
| | 1000 | 0 | — |
| Nicosulfuron + Topramezone + Dimethenamid-P | 30 + 20 + 500 | 75 | 48 |
| | 30 + 20 + 1000 | 75 | 48 |
| | 30 + 50 + 500 | 80 | 69 |
| | 30 + 50 + 1000 | 80 | 69 |

Test Example 4

Upland field soil was put into a 1/160,000 ha pot, and seeds of wild oat (*Avena fatua* L.) were sown. On the next day, predetermined amounts of ONEHOPE NYUZAI (tradename), Clio (tradename) and Spectrum (tradename) were diluted with water (in an amount corresponding to 300 L/ha) and applied for soil treatment by a small sprayer.

On the 28 th day after treatment, the state of growth of the wild oat was visually observed to determine the growth inhibition rate (%). The growth inhibition rate (%) (measured value) and the growth inhibition rate (%) calculated in the same manner as in the above Test Example 1 are shown in Table 4.

TABLE 4

| Compound | Dose (g/ha) | Growth inhibition rate of wild oat (%) | |
|---|---|---|---|
| | | Measured value | Calculated value |
| Nicosulfuron | 100 | 60 | — |
| Topramezone | 15 | 0 | — |
| Dimethenamid-P | 250 | 60 | — |
| Nicosulfuron + Topramezone + Dimethenamid-P | 100 + 15 + 250 | 93 | 84 |

Industrial Applicability

The herbicidal composition of the present invention has a broad herbicidal spectrum, has high activity and has a long lasting effect, broadening of the herbicidal spectrum particularly against *gramineae* and application to genetically-modified crops resistant to ALS inhibitors, etc. are possible, an increase in the application site can be expected, and thus it is useful as a herbicidal composition.

Further, the herbicidal composition of the present invention is very useful such that development of resistance is to be delayed by use of active ingredients differing in the mechanism in combination, against weeds which have acquired resistance due to repeated application of a specific herbicide.

The entire disclosure of Japanese Patent Application No. 2012-120607 filed on May 28, 2012 including specification, claims and summary is incorporated herein by reference in its entirety.

The invention claimed is:

1. A herbicidal composition comprising in combination, (a) nicosulfuron or its salt, (b) dimethenamid-P or its salt and (c) topramezone or its salt, wherein the mixing ratio of (a) to (b) is from 1:2.5 to 1:150 by the weight ratio, and the mixing ratio of (a) to (c) is from 6.7:1 to 1:10 by the weight ratio.

2. The herbicidal composition according to claim 1, which is used to control *convolvulaceae, solanaceae, gramineae, malvaceae, compositae* or *leguminosae*, or to inhibit their growth.

3. A method for controlling undesired plants or inhibiting their growth, which comprises applying a herbicidally effective amount of a herbicidal composition comprising, in combination, (a) nicosulfuron or its salt, a herbicidally effective amount of (b) dimethenamid-P or its salt, and a herbicidally effective amount of (c) topramezone or its salt, to the undesired plants or to a place where they grow, wherein (a) is applied in an amount of from 10 to 100 g/ha, (b) is applied in an amount of from 250 to 1,500 g/ha, and (c) is applied in an amount of from 15 to 100 g/ha.

4. The method according to claim 3, wherein the undesired plants are *convolvulaceae, solanaceae, gramineae, malvaceae, compositae* or *leguminosae*.

5. The method according to claim 3, wherein the undesired plants are *gramineae, malvaceae, compositae* or *leguminosae*.

6. The method according to claim 3, wherein the undesired plants are annual or perennial *gramineae*.

7. The method according to claim 3, wherein the undesired plants are strongly noxious weeds in corn fields.

8. The method according to claim 3, wherein the undesired plants are annual and perennial *gramineae* selected from the group consisting of *Echinochloa* spp., *Digitaria* spp., *Setaria* spp., *Poa* spp., *Avena* spp., *Agropyron* spp., *Alopecurus* spp., *Eleusine* spp., *Rottboellia* spp., *Sorghum* spp. and *Panicum* spp., which are problematic as noxious weeds in corn fields.

* * * * *